United States Patent [19]

Langford

[11] 4,207,310

[45] Jun. 10, 1980

[54] IODINE-AMINE OXIDE DISINFECTANTS

[75] Inventor: Philip W. Langford, Longwell Green, England

[73] Assignee: Tenneco Chemicals, Inc., Saddle Brook, N.J.

[21] Appl. No.: 839,229

[22] Filed: Oct. 4, 1977

Related U.S. Application Data

[63] Continuation-in-part of Ser. No. 635,396, Nov. 26, 1975, abandoned.

[30] Foreign Application Priority Data

Nov. 29, 1974 [GB] United Kingdom ............... 51844/74
Aug. 28, 1975 [GB] United Kingdom ............... 35552/75

[51] Int. Cl.$^2$ ............................................. A61L 13/00
[52] U.S. Cl. .................................... 424/150; 424/263; 424/330; 252/106
[58] Field of Search ........................................ 424/150

[56] References Cited

U.S. PATENT DOCUMENTS

| | | | |
|---|---|---|---|
| 3,028,299 | 4/1962 | Wimcov et al. | 424/150 |
| 3,240,711 | 3/1966 | Wittwer | 252/106 |
| 3,380,923 | 4/1968 | Beach | 424/150 |
| 3,534,102 | 10/1970 | Waldstein | 260/584 |

OTHER PUBLICATIONS

Kirk–Othmer—Encyclopedia of Chemical Technology, 2nd ed., pp. 32 & 33, (1971).
"Miscellaneous Non-Ionic Surfactants", L. W. Burnette, pp. 403–404.
McCutcheon's Detergents & Emulsifiers, p. 65, 1971.
Chemical Abstracts 62:13034g (1965).

*Primary Examiner*—Leonard Schenkman
*Attorney, Agent, or Firm*—James P. Scullin

[57] ABSTRACT

Improved iodine-containing compositions suitable for use in combating bacteria, fungi, viruses, yeasts, and other undesirable micro-organisms are provided by the use of certain tertiary amine oxides as solubilizers or co-solubilizers for iodine. The compositions may also comprise surfactants, iodides, acids, and liquid media. The compositions are stable and effective, and may be low-foaming.

20 Claims, No Drawings

IODINE-AMINE OXIDE DISINFECTANTS

This is a continuation-in-part of my copending application Ser. No. 635,396 filed Nov. 26, 1975 now abandoned.

SUMMARY OF THE INVENTION

This invention relates to novel compositions which have particular value in combatting micro-organisms and in sterilising and disinfecting surfaces, instruments, utensils and other objects which may have come in contact with such micro-organisms including pathogenic bacteria, fungi, viruses and yeasts. In particular, the invention provides improved iodophors which combine the desirable features of long term stability, a high level of bactericidal and fungicidal activity against a wide spectrum of pathogenic micro-organisms, and particularly high activity against acid fast bacteria. In one preferred embodiment, the invention provides improved iodophors which combine low foaming propensity with the other desirable features.

The novel compositions of this invention comprise iodine solubilized with certain tertiary amine oxides, and optionally with other ingredients.

The invention also relates to methods for the preparation of such useful iodophors and to their use for bactericidal and fungicidal purposes.

BACKGROUND OF THE INVENTION

The high germicidal activity of elemental iodine is well known, but its low solubility in water (1 part in 3,450 at 20° C.) militates against its use in aqueous antiseptics. It is used in aqueous alcohol solution as tincture of iodine, but such preparations are not suitable for sterilizing surfaces, instruments, utensils etc. and when used as disinfectants on open wounds, cuts and abrasions, cause irritation and dicomfort due to the rapid evaporation of the alcohol and precipitation of the iodine. Moreover, such preparations cause undesirable staining of the skin or other surfaces with which they come in contact.

Cantor and Shelansky in 1951 discovered that certain surfactants had the property of complexing with elemental iodine to yield molecular aggregates or micelles which on dilution with water yielded the free iodine in a germicidally active form. Such complexes were termed 'iodophors' and they have become important commercial disinfectants and sterilizing agents.

An inspection of the voluminous patent literature relating to iodophor compositions makes it clear that many surfactants are capable of solubilising iodine. Thus, quaternary ammonium compounds are disclosed for this purpose in British patent specification No. 625,676. (West Laboratories Inc.); long chain alkyl phenol-ethylene oxide condensates are the non-ionic surfactants employed in the compositions covered by British patent specification No. 950,954 (West Laboratories, Inc.), in U.S. Pat. No. 2,989,434, (G. A. Brost, F. Krupkin and F. Woodward) and in British patent specification No. 923,114 (W. C. Evans & Co.). Condensates of ethylene oxide and aliphatic ethers or glycols are the preferred non-ionic surfactants employed as iodine solubilisers in the compositions referred to in U.S. Pat. No. 3,326,806 (G. P. Dolby) and in Netherlands patent application No. 64.12604 (W. C. Evans & Co.). Anionic surfactants have also been employed as iodine solubilisers, for example, in the iodophor compositions featured in U.S. Pat. No. 3,650,966 (R. L. Bakka) and 3,240,711 (G. C. Wittwer).

Mixtures of surfactants have also been employed, e.g. the mixture of poly-(vinyl pyrrolidine) and ethoxylated nonyl alcohol in German Offen. 2,105,057 (A. Halpern).

Other publications which disclose iodine/surfactant combinations include: British patent specifications Nos. 703,091 (General Aniline & Film Corp.); 962,955 (Bendix Corp.); 1,004,282 (West Laboratories, Inc.); 1,066,437 (W. C. Evans & Co.); 1,167,743 (West Laboratories. Inc.); 1,293.407 (BASF Wyandotte Corp.); and 1,311,952 (Marles-Kuhlemann-Wyandotte.) Iodine/amine compositions are disclosed in British patent specification Nos. 1,186,177 (Diversey Development Ltd.) and 1,316,571 (Dipenidam Ltd.).

In general, non-ionic surfactants have been preferred since the germicidal action of iodophors formulated with them is less adversely affected by the hardness of the water used to dilute them for use.

For many purposes it is desirable that iodophors, when diluted to the concentration in which they are used, should not foam to any great extent and the minimising of the foaming propensity is frequently the reason for the choice of a particular surfactant or surfactant mixture even though the germicidal properties and/or storage stability may not be so good as might be achieved by similar compositions formulated with other surfactants. It is a feature of one preferred embodiment of the invention to which this patent relates that it provides iodophors which combine low foaming properties and a high degree of germicidal activity.

Not all the elemental iodine complexed in iodophor compositions is made available on dilution and it is a very desirable feature of such compositions that the ratio of available iodine (as determined by titration with standard thiosulphate solution) to total iodine should be as close to unity as possible without creating instability and that this ratio should not be reduced significantly on storage. The compositions to which this patent relates are characterized by a high ratio of available to total iodine and excellent storage stability. Furthermore they contain a greater percentage of both total and available iodine than the great majority of commercial iodophors.

The germicidal activity of elemental iodine, it is known, is enhanced at low pH, and iodophors are generally formulated with the addition of an acid. Because of its good anticorrosion properties and buffering action, phosphoric acid is particularly useful in this respect. In one embodiment of this invention, a mixture of sulphuric acid and phosphoric acid is used to control the pH at or near the optimum level.

Hitherto, it has been found that the germicidal action of diluted iodophors is due solely to the elemental iodine released and that the activity of iodophor disinfectants can be accurately predicted from the known activity of aqueous or aqueous/alcohol solutions of iodine of similar iodine concentration.

I have now found that the use of certain tertiary amine oxides as solubilisers or co-solubilisers confers a synergistic bacterial action on iodophor compositions to give formulations which are much more active against certain pathogens, particularly the acid fast bacteria, than any hitherto disclosed iodophor.

In addition, the use of certain low foaming surfactants with these tertiary amine oxides gives compositions which have desirable low-foaming properties.

A further advantage of the compositions to which this patent relates is that the tertiary amine oxide functions as a stabilizer as well as a synergistic solubilizing agent in combination with surfactants, and such compositions show a high and stable ratio of active to total iodine.

DETAILED DESCRIPTION OF THE INVENTION

The tertiary amine oxides suitable for use in the compositions according to this invention are those having the general formula:

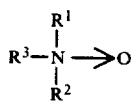

where $R^1$ and $R^2$ are methyl groups or ethyl groups and are the same or different, and $R^3$ is a phenyl group or methyl-substituted phenyl group, a benzyl group or methyl-substituted benzyl group, a cyclohexyl group or methyl-substituted cyclohexyl group, a cyclohexanemethyl group or methyl-substituted cyclohexanemethyl group; or where $R^1$ is a methyl group or an ethyl group and N, $R^2$ and $R^3$ together form part of a saturated or unsaturated heterocyclic group, or where N, $R^1$, $R^2$, and $R^3$ together form part of a saturated or unsaturated heterocyclic group or bridged heterocyclic group.

When N, $R^2$, and $R^3$, or N, $R^1$, $R^2$, and $R^3$, form a heterocyclic or bridged heterocyclic group, a second tertiary amine oxide group can also optionally be included in the heterocyclic or bridged heterocyclic group.

Examples of suitable tertiary amine oxides include: N, N-dimethyl benzylamine oxide; N, N-diethyl benzylamine oxide; N-methyl N-ethyl benzylamine oxide; pyridine N-oxide; α-picoline N-oxide; β-picoline N-oxide; γ-picoline N-oxide; pyrazine N-oxide; pyrazine N, N'-dioxide; N-methyl piperidine N-oxide; N-ethyl piperdine N-oxide; N-methyl piperazine N-oxide; N, N' dimethyl piperazine N, N'-dioxide; triethylenediamine N-oxide; triethylenediamine N, N'-dioxide; N-ethyl morpholine N-oxide; N-methyl morpholine N-oxide; quinoline N-oxide; N-methyl pyrrole N-oxide; N-methyl pyrrolidine N-oxide; N, N-dimethyl cyclohexylamine N-oxide; N, N-dimethyl cyclohexanemethylamine N-oxide; and N, N-dimethylaniline N-oxide.

As will be apparent from the foregoing general formula, the tertiary amine oxides useful in the practice of the present invention are those having at least one cyclic group as a substituent on the nitrogen atom or forming a part of such a substituent, and those in which the nitrogen atom forms a part of a heterocyclic group. In addition, these tertiary amine oxides are not effective surfactants, i.e. they do not drastically reduce the surface tension of water when in dilute aqueous solution.

I prefer to use a single tertiary amine oxide in making the novel disinfectant compositions, or iodophors, of this invention, but mixtures of two or more can be employed if desired.

Although useful disinfectant compositions can be prepared using a tertiary amine oxide as the sole solubilizer for iodine, these embodying the broadest scope of the invention, it is preferred to employ a surfactant as a co-solubilizer.

As co-solubilizer in conjunction with the claimed tertiary amine oxides, non-ionic surfactants are preferred. Particularly useful nonionic surfactants are the condensation products of ethylene oxide, or combination of ethylene oxide and propylene oxide, with long chain aliphatic alcohols. However, it is known that a variety of anionic, cationic and nonionic surfactants can act as iodine solubilizers and it is not intended that the scope of this invention should be limited to particular types of surfactants or mixtures. Thus, the co-solubilizer can be one or more nonionic, anionic, or cationic surfactant or any combatible mixture thereof. The essential feature is the inclusion, with the co-solubilizer, of a tertiary amine oxide. The tertiary amine oxide functions not only as a solubilizer of iodine, but also to enhance the stability as shown by maintaining the amount of available iodine, and to enhance the microbicidal activity of the composition.

A preferred class of nonionic surfactants comprises the condensation of fatty alcohol having from about 8 to about 20 carbon atoms, and especially from about 10 to about 15 carbon atoms, with from about 8 to about 12 moles of ethylene oxide or with a combination of ethylene oxide and propylene oxide. For applications in which a disinfectant having a high propensity to foam is not a disadvantage, or in which foaming is desirable, nonionic surfactants prepared with ethylene oxide are preferred. Where it is desired to prepare a non-foaming disinfectant, or one with a low propensity to foam, nonionic surfactants made with a combination of ethylene oxide and propylene oxide are preferred. Such low foaming iodophors represent a particularly preferred embodiment of the present invention.

For the preparation of high-foaming iodophors, a particularly preferred nonionic surfactant is one made by condensing n-decanol with 9 moles of ethylene oxide.

For the preparation of low-foaming iodophors, preferred nonionic surfactants are those prepared by condensing one mole of an aliphatic alcohol with from about 4 to about 7 moles of propylene oxide and with an amount of ethylene oxide ranging from 1 to 4 times the amount of propylene oxide, on a molar basis. Examples of suitable surfactants for this purpose are products sold by BASF under the tradenames LUTENSOL LF 401 and LUTENSOL LF 700.

The iodophor compositions which are the subject of this invention function most effectively at low pH, and it is a preferred feature of these compositions that sufficient acid selected from the group consisting of hydrochloric acid, sulphuric acid, phosphoric acid, sulphamic acid, hydroxyacetic acid and citric acid or mixtures thereof, is incorporated so that a 1% aqueous solution has a pH of 6 or less, preferably between 1 and 4.

Particularly preferred is a mixture having a weight ratio of about 3 parts of sulphuric acid and about 2 parts of phosphoric acid. In place of the foregoing preferred acids, any water soluble acid can be used without departing from the scope of this invention.

The compositions can, optionally and advantageously, also include a minor amount of at least one water-soluble iodide selected from the group consisting of hydrogen iodide and inorganic iodides, such as potassium iodide, sodium iodide, or calcium iodide. Potassium iodide is preferred.

The iodine concentrate comprising the iodine dissolved in the surfactant-amine oxide mixture and containing the added acid, and if desired, the water soluble iodide, is dissolved for use in a liquid medium. Generally, this is water and the production and use of aqueous solutions of iodophors claimed for sterilising and disinfecting surfaces, instruments, utensils, and other objects is a particular feature of this invention. For certain purposes, a monohydric, dihydric, or polyhydric alcohol, or a mixture of these or aqueous solutions of these or their mixtures, may be preferred as the diluting medium. Examples of suitable liquid media, in addition to water, include isopropanol, ethylene glycol, and glycerol.

The ratio of iodine to tertiary amine oxide is not critical, and can be varied over a wide range. It is essential to use sufficient of the tertiary amine oxide to dissolve the iodine and to keep it in solution when the composition is diluted with a liquid medium for use as a disinfectant. An excess of tertiary amine oxide, over that necessary to dissolve the iodine, can be used if desired although it is preferred not to employ a substantial excess because of the cost involved. It is believed that those skilled in the art will have no difficulty in determining the minimum amount of a given tertiary amine oxide required to dissolve a given amount of iodine, with only a minimum amount of routine experimentation.

When preparing an iodophor using a surfactant as co-solubiliser, an acid, and a liquid medium according to this invention, the relative proportions of each ingredient are not critical and can be varied over wide limits. It is preferred to use from about 0.5 to about 6 percent by weight of iodine, from about 2 to about 12 percent by weight of tertiary amine oxide, from about 20 to about 30 percent by weight of surfactant, from about 1 to about 50 percent of acid, and the balance of from about 2 percent to about 76.5 percent by weight of liquid medium. The amount of acid should be sufficient that the pH of a 1% by weight aqueous solution of the iodophor composition is 6 or less, and preferably between 1 and 4.

Amounts of these ingredients which fall outside of the foregoing preferred limits can be used if desired without departing from the scope of this invention. The only critical limitation is the use of enough of the combination of tertiary amine oxide and surfactant to dissolve the iodine and maintain it in solution, and enough tertiary amine oxide to obtain the benefits of improved retention of the amount of available iodine during storage, and improved microbicidal activity.

When a water soluble iodide is employed, it is preferred that the amount be from about 0.3 to about 5 percent by weight based on the total weight of the iodophor composition. Greater or lesser amounts can be used if desired, without departing from the scope of this invention.

In preparing the compositions of this invention, the order of addition of the various ingredients is not critical, but can be varied as desired. For example, iodine and a tertiary amine oxide can be stirred together at room temperature, or at an elevated temperature, until complete solution has been effected. If desired, the solution can then be diluted with a suitable liquid medium.

Alternatively, the amine oxide can first be diluted with a liquid medium, e.g. water, and the iodine can then be dissolved in the mixture.

When a surfactant is used as a co-solubiliser, the iodine can be dissolved in the tertiary amine oxide and the surfactant added subsequently; or the iodine can be dissolved in the surfactant, followed by the addition of the tertiary amine oxide; or the iodine can be dissolved in a mixture of surfactant and tertiary amine oxide. The liquid medium can be added at any convenient stage, before or after the addition of iodine. Once a homogeneous solution has been obtained, sufficient acid is added to bring the pH of a 1% by weight aqueous solution to 6 or less, preferably between 1 and 4. When a water soluble iodide is used it can be added to the composition at any convenient stage, although it is preferred to add it last.

A preferred method of preparation is to dissolve the iodine in the surfactant, add the tertiary amine oxide and stir until homogeneous, add the acid and the liquid medium, and then add the water soluble iodide.

The compositions can be analyzed for total iodine and for available iodine by any suitable analytical procedure, such procedures being well known to those skilled in the art. For the determinations of available iodine, I prefer titration with standardized sodium thiosulphate.

For use in destroying undesirable micro-organisms and for sterilizing and disinfecting surfaces, instruments, utensils and other objects, the iodine containing compositions or iodophors of this invention are generally employed as dilute solutions, preferably in water although other solvents can be used if desired. To accomplish the desired result, the dilute solution is applied to the surface, or the object to be disinfected is dipped into such a dilute solution for a sufficient period of time, or the dilute solution is otherwise applied to a locus contaminated with micro-organisms.

The following examples illustrate the invention, but are not to be considered limitative thereof.

EXAMPLE 1

5 Parts of elemental iodine are added to 28.5 parts of a non-ionic surfactant made by condensing 9 moles of ethylene oxide with one mole of decyl alcohol and having the formula $C_{10}H_{21}-(CH_2-CH_2-O)_9H$, and the mixture is stirred at between 30° and 40° until dissolved. To this solution is added 6 parts of N,N-dimethyl benzylamine N-oxide and this mixture is stirred at a temperature below 40° C. until homogeneous. Then 12 parts of sulphuric acid and 8 parts of phosphoric acid in 32.5 parts of water are added to give an iodophor concentrate containing 4.4% of active iodine.

EXAMPLE 2

0.4 Parts by weight of potassium iodide are stirred into 100 parts by weight of the composition prepared according to Example 1 to yield an iodophor composition containing 4.6% available iodine.

EXAMPLE 3

3.0 Parts of elemental iodine are dissolved in a mixture of 4.0 parts of Lutensol LF401 and 13.0 parts Lutensol LF700 at 45°-50° C. Lutensol LF401 and LF700 are condensates of fatty alcohol and ethylene and propylene oxide. 3.5 parts of a 32.6% aqueous solution of N.N.-dimethyl benzyl amine, N-oxide are added with stirring. The mixture is cooled and a blend of 54 parts phosphoric acid and 22.5 parts isopropanol added with stirring. This yields an iodophor concentrate containing 1.9% available iodine.

EXAMPLE 4

In the same manner as for Examples 1 and 3 an iodophor composition containing 2.1% available iodine was prepared by dissolving 2.4 parts of iodine in 25.1 parts of the non-ionic surfactant used in Example 1, then adding 2.8 parts of pyridine-N-oxide and adjusting the pH by the addition of 12 parts of sulphuric acid, 8 parts of phosphoric acid and 49.7 parts of water.

EXAMPLE 5

As for example 4, an iodophor composition containing 4.4% available iodine is prepared from 5.1 parts of iodine, 28.9 parts non-ionic detergent $C_{10}H_{21}O-(C_2H_4O)_9H$, 10 parts of α-picoline-N-oxide 12 parts sulphuric acid, 8 parts of phosphoric acid and 35 parts of water.

EXAMPLE 6

This is a comparative example, prepared according to the prior art, without tertiary amine oxide. In this example, 2.7 parts of idoine are dissolved in 13.5 parts of a nonyl phenol/ethylene oxide condensate. To this solution is added 2.0 parts of a solution of an alkyl quaternary ammonium chloride in isopropanol and water, 7.5 parts of phosphoric acid, 13.0 parts of sulfuric acid and 61.3 parts of water. This yields an iodophor having an available iodine concentration of 2.16%.

In the foregoing examples, and in all other examples, the expression "parts" refers to parts by weight unless otherwise specified.

The following test methods were used to evaluate the properties of the products of Examples 1-6. For comparative purposes, three commercially available iodophors which do not contain tertiary amine oxides were included in these tests. The results are summarized in Table I.

Methods of Test

1. Bacteriostatic and Fungistatic Activity in Nutrient Agar

To establish the minimum concentration of the preparation to inhibit growth of a test organism on an agar surface.
Test Organisms
*Staph. aureus* (NCTC 4163)
*E. coli* (NCTC 5934)
*Ps. aeruginosa* (NCTC 6749)
*C. albicans* (ATCC 10231)
Nutrient broth cultures of each organism were maintained at 37° C. before use. Dilutions of the preparation under test were prepared in molten nutrient agar, poured in petri dishes and allowed to set. Discrete areas of the agar surfaces were inoculated with the test organisms by means of a platinum loop and all plates were incubated at 37° C. for 48 hours before being examined for growth.

2. For Bactericidal Activity Against *Salmonella choleraesuis*

This test for general purpose disinfectant is carried out according to the instructions given in the Section 3 (1) of the "Explanatory Note on the Approval of Disinfectants for the Purpose of the Diseases of Animals" Act 1950, published by the British Government's Ministry of Agriculture, Fisheries and Food. The effective concentration of the disinfectant is that which, when added to a cold yeast suspension containing 4% of an active culture of *S. choleraesuis* at 4°±0.5° C. inhibits growth of the organism. No growth in two or more of the five samples is regarded as a pass; growth in more than three constitutes a failure.

3. For Bactericidal Activity Against *Mycobacterium foruitum*

The method outlined in Section 3 (2) of the Ministry of Agriculture note referred to in the last paragraph was employed. This is similar to the test against *S. choleraesuis* but employs a 7-day old active culture of *Mycobacterium fortuitum* (N.C.T.C. No. 8579, N.C. I.B. 10384) as the test organism.

4. Test for Foaming Properties 150 ml of the solution to be tested (a use dilution of a composition containing 6 to 25 ppm of available iodine) is placed in a 500 ml calibrated gas washing bottle with fritted cylinder. Using an air flow meter, the air flow is adjusted to 2 liters per minute and the foam height is read after equilibrium has been established at a temperature of 25° C. (Method described in U.S. Pat. No. 3,525,696).

5. Test for Storage Stability

The iodophor is tested for the percentage of active iodine by titration with standard thiosulphate solution when freshly prepared and after one year storage in a closed container at room temperature.

The results in Table I show that Examples 1-5 made according to the invention have significantly and unexpectedly greater activity against *C. albicans, S. choleraesius* and *M. fortuitum* than do Example 6 made according to the prior art and the three commercial iodophors. Examples 1-5 also show excellent retention of % available iodine after aging for a year. Example 3, made according to a preferred embodiment of the present invention, combines a very low propensity to foam with high microbicidal activity and excellent retention of % available iodine.

EXAMPLES 7-14

One part of iodine is dissolved in 10 parts of the following tertiary amine oxides:

| Example | Tertiary Amine Oxide |
|---|---|
| 7 | pyridine N-oxide |
| 8 | α-picoline N-oxide |
| 9 | N,N-dimethyl cyclohexylamine N-oxide |
| 10 | N-methyl piperidine N-oxide |

TABLE I

| Iodophor | Minimum Inhibitory Conc. against (μg/ml available iodine) | | | | Pass Dilution (UK Ministry of Agriculture method) against | | Foam Rating ml | % Available Iodine | |
|---|---|---|---|---|---|---|---|---|---|
| | Staph aureus | E. coli | Ps aeruginosa | C. albicans | S. cholergesuis | M. fortuitum | | Initial | After 1 year |
| Example 1 | 31 | 62 | 62 | 31 | 1-250 | 1-250 | >550 | 4.4 | 4.25 |
| Example 2 | 31 | 31 | 62 | 31 | 1-300 | 1-250 | >550 | 4.6 | 4.4 |
| Example 3 | 31 | 31 | 31 | 31 | 1-170 | 1-170 | 25 | 1.9 | 1.7 |
| Example 4 | 31 | 31 | 31 | 31 | 1-170 | 1-160 | >550 | 2.1 | 2.0 |
| Example 5 | 31 | 31 | 31 | 31 | 1-300 | 1-300 | >550 | 4.6 | 4.4 |

TABLE I-continued

| Iodophor | Minimum Inhibitory Conc. against (μg/ml available iodine) | | | | Pass Dilution (UK Ministry of Agriculture method) against | | Foam Rating ml | % Available Iodine | |
|---|---|---|---|---|---|---|---|---|---|
| | Staph aureus | E. coli | Ps aeruginosa | C. albicans | S. cholerqesuis | M. fortuitum | | Initial | After 1 year |
| Example 6 | 31 | 31 | 31 | 62 | 1–85 | 1–30 | >550 | 2.16 | 1.95 |
| Dyne (Ciba Geigy Ltd.) | 31 | 31 | 31 | 62 | 1–85 | 1–90 | 50 | 1.6 | — |
| Phiodin (Phosyn Ltd.) | 31 | 31 | 31 | 125 | 1–90 | 1–11 | >550 | 2.1 | — |
| FAM 30 (Vanodine Ltd.) | 31 | 31 | 62 | 62 | 1–180 | 1–30 | >550 | 2.6 | — |

| Example | Tertiary Amine Oxide |
|---|---|
| 11 | N-methyl pyrrolidine N-oxide |
| 12 | N-methyl piperazine N-oxide |
| 13 | quinoline N-oxide |
| 14 | N,N-dimethyl benzylamine N-oxide |

When diluted with water, the product of each example is found to have efficacy as a disinfectant, with the best results given by the products of Examples 7, 8, and 14.

EXAMPLE 15

A composition according to the invention was prepared by dissolving 1.66 parts of iodine in 16.6 parts of pyridine N-oxide. This solution was then further diluted with 40 parts of 2-propanol, 0.5 parts of orthophosphoric acid and 41.24 parts of water.

The product had 1.61% available iodine.

When tested by the methods previously described, the product had a pass dilution of 1/60 against S. choleraesius and 1/100 against M. fortuitum.

EXAMPLE 16

An iodophor composition according to the invention was prepared by dissolving 4.75 parts of iodine in a mixture of 21.3 parts of a nonionic surfactant prepared by condensing 9 moles of ethylene oxide with 1 mole of n-decanol, 5.4 parts of a nonionic surfactant prepared by condensing 5 moles of ethylene oxide with 1 mole of a mixture of straight chain aliphatic alcohol, having 10–12 carbon atoms, and 19.8 parts of a 30% aqueous solution of N, N-dimethyl benzylamine N-oxide. After solution was complete, 8.8 parts of orthophosphoric acid, 14.3 parts of sulfuric acid, and 25.65 parts of water were added and the mixture was stirred until it was homogeneous.

The product of this example had an available iodine content of 4.2%. When tested by the methods previously described, it had a pass dilution of 1/250 against S. choleraesius, and 1/140 against M. fortuitum.

EXAMPLE 17

An iodophor was prepared according to the invention by dissolving 12.6 parts of iodine in 53.55 parts of LUTENSOL LF700 and 17.85 parts of LUTENSON LF401 (condensates of fatty alcohol with a combination of ethylene oxide and propylene oxide). To this solution was added 40.4 parts of a 32.6% aqueous solution of N,N-dimethyl benzylamine N-oxide, with stirring. When the solution was homogeneous 200 parts of concentrated phosphoric acid and 75.6 parts of isopropanol were added and the mixture was again stirred until it was homogeneous.

EXAMPLE 18

This is a comparative example, made according to the prior art, without tertiary amine oxide.

A solution of 2.98 parts of iodine in 16.78 parts of LUTENSOL LF700 was prepared, and was blended with a solution of 1.73 parts of iodine in 9.76 parts of LUTENSOL LF401. To this blend was added 100 parts of concentrated phosphoric acid and 87 parts of isopropanol, and the mixture was stirred until it was homogeneous.

Separate portions of the products of Examples 17 and 18 were stored at room temperature and at 40° C., and were analyzed at various time intervals for % available iodine by titration with sodium thiosulphate. The results are summarized in Table II, and demonstrate the improved stability of the product of Example 17 which contain a tertiary amine oxide.

TABLE II

| | EXAMPLE 17 | | | | EXAMPLE 18 | | | |
|---|---|---|---|---|---|---|---|---|
| | ROOM TEMPERATURE | | 40° C. | | ROOM TEMPERATURE | | 40° C. | |
| DAYS AGED | % AVAILABLE IODINE | % LOSS | % AVAILABLE IODINE | % LOSS | % AVAILABLE IODINE | % LOSS | % AVAILABLE IODINE | % LOSS |
| 1 | 2.375 | — | 2.285 | — | 1.7 | — | 1.7 | — |
| 3 | 2.273 | 4.3 | — | — | — | — | — | — |
| 5 | — | — | — | — | 1.63 | 4.1 | 1.54 | 9.4 |
| 7 | — | — | 2.200 | 3.7 | — | — | — | — |
| 26 | — | — | — | — | 1.55 | 8.8 | — | — |
| 28 | 2.272 | 4.3 | — | — | — | — | — | — |
| 32 | — | — | — | — | — | — | 1.49 | 12.1 |
| 36 | — | — | 2.16 | 5.5 | — | — | — | — |

I claim:

1. A composition comprising iodine dissolved in a tertiary amine oxide selected from the group consisting of N,N-dimethyl benzylamine N-oxide, pyridine N-oxide, and picoline N-oxides, in relative proportions of from about 0.05 to about 6 parts by weight of iodine and from about 2 to about 12 parts by weight of tertiary amine oxide.

2. A composition as in claim 1 which also comprises: a liquid medium selected from the group consisting of water, monohydric alcohols, polyhydric alcohols, and mixtures thereof; and an acid selected from the group consisting of hydrochloric acid, sulfuric acid, phosphoric acid, sulfamic acid, hydroxyacetic acid, citric acid and mixtures thereof, in relative proportions of from about 2 to about 76.5 parts by weight of said liquid medium and from about 1 to about 50 parts by weight of said acid.

3. A composition as in claim 1 which also comprises from about 20 to about 30 parts by weight of at least one nonionic surfactant made by the condensation of ethylene oxide or combinations of ethylene oxide and propylene oxide with long chain aliphatic alcohols.

4. A composition as in claim 2 which also comprises from about 20 to about 30 parts by weight of at least one nonionic surfactant made by the condensation of ethylene oxide or combinations of ethylene oxide and propylene oxide with long chain aliphatic alcohols.

5. A composition as in claim 2 which also comprises at least one iodide selected from the group consisting of HI and water-soluble inorganic iodides in an amount of from about 0.3 percent to about 5 percent based on the total weight of said composition.

6. A composition as in claim 5 wherein the iodide is potassium iodide.

7. A composition as in claim 1 wherein the tertiary amine oxide is N,N-dimethyl benzylamine N-oxide.

8. A composition as in claim 1 wherein the tertiary amine oxide is pyridine N-oxide.

9. A composition as in claim 1 wherein the tertiary amine oxide is alpha-picoline N-oxide.

10. A composition as in claim 2 which contains sufficient acid that a 1% by weight aqueous solution of said composition has a pH of 6 or less.

11. A composition as in claim 10, wherein the pH of a 1% by weight aqueous solution is between 1 and 4.

12. A composition as in claim 4 wherein the surfactant is a nonionic surfactant comprising the condensation product of one or more fatty alcohols having from 8 to 20 carbon atoms with from about 9 to about 12 moles of ethylene oxide per mole of alcohol.

13. A composition as in claim 12 wherein the surfactant is the condensation product of one mole of n-decanol and 9 moles of ethylene oxide.

14. A composition as in claim 4 wherein the surfactant is a low foaming nonionic surfactant comprising the condensation product of a fatty alcohol having from about 8 to about 20 carbon atoms with ethylene oxide and propylene oxide.

15. A composition according to claim 4 which comprises from about 0.5 to about 6 percent by weight of iodine, from about 2 to about 12 percent by weight of said tertiary amine oxide, from about 20 to about 30 percent by weight of said surfactant, from about 1 to about 50 percent by weight of said acid, and from about 2 to about 76.5 percent by weight of said liquid medium.

16. A composition as in claim 15 which also comprises from about 0.3 to about 5 percent by weight of an iodide selected from the group consisting of HI and water-soluble inorganic iodides.

17. A composition according to claim 15 wherein said acid is a mixture of sulfuric acid and phosphoric acid in a weight ratio of about 3 parts of sulfuric acid to about 2 parts of phosphoric acid.

18. A process for the control of micro-organisms in a locus which comprises applying to the locus a disinfecting amount of the composition of claim 1.

19. A process for the control of micro-organisms in a locus which comprises applying to the locus a disinfecting amount of the composition of claim 2.

20. A process for the control of micro-organisms in a locus which comprises applying to the locus a disinfecting amount of the composition of claim 4.

* * * * *